United States Patent
Suzuki et al.

(10) Patent No.: US 10,786,435 B2
(45) Date of Patent: Sep. 29, 2020

(54) COMPOSITION FOR OPTICAL THREE-DIMENSIONAL MODELING

(71) Applicant: KURARAY NORITAKE DENTAL INC., Kurashiki-shi (JP)

(72) Inventors: Kenji Suzuki, Niigata (JP); Naoki Nishigaki, Niigata (JP)

(73) Assignee: KURARAY NORITAKE DENTAL INC., Kurashiki-shi (JP)

( * ) Notice: Subject to any disclaimer, the term of this patent is extended or adjusted under 35 U.S.C. 154(b) by 0 days.

(21) Appl. No.: 16/343,923

(22) PCT Filed: Oct. 13, 2017

(86) PCT No.: PCT/JP2017/037260
§ 371 (c)(1),
(2) Date: Apr. 22, 2019

(87) PCT Pub. No.: WO2018/074380
PCT Pub. Date: Apr. 26, 2018

(65) Prior Publication Data
US 2019/0254936 A1    Aug. 22, 2019

(30) Foreign Application Priority Data

Oct. 21, 2016 (JP) ................. 2016-207184

(51) Int. Cl.
| | | |
|---|---|---|
| *C08F 2/46* | (2006.01) | |
| *C08F 2/50* | (2006.01) | |
| *C08G 61/04* | (2006.01) | |
| *A61K 6/887* | (2020.01) | |
| *C08K 3/014* | (2018.01) | |
| *C08K 5/00* | (2006.01) | |
| *C08K 5/3475* | (2006.01) | |
| *C08K 9/04* | (2006.01) | |
| *C08F 2/44* | (2006.01) | |
| *A61K 6/62* | (2020.01) | |
| *A61K 6/71* | (2020.01) | |
| *A61K 6/80* | (2020.01) | |
| *A61K 6/84* | (2020.01) | |

(52) U.S. Cl.
CPC ................ *A61K 6/887* (2020.01); *A61K 6/62* (2020.01); *A61K 6/71* (2020.01); *A61K 6/80* (2020.01); *A61K 6/84* (2020.01); *C08F 2/44* (2013.01); *C08K 3/014* (2018.01); *C08K 5/005* (2013.01); *C08K 5/3475* (2013.01); *C08K 9/04* (2013.01)

(58) Field of Classification Search
CPC .... A61K 6/083; A61K 6/0073; A61K 6/0052; C08K 9/04; C08K 5/005; C08K 5/3475; C08K 3/014
USPC ........... 522/75, 74, 71, 189, 184, 6, 1; 520/1
See application file for complete search history.

(56) References Cited

U.S. PATENT DOCUMENTS

| | | |
|---|---|---|
| 5,849,459 A | 12/1998 | Hagiwara et al. |
| 2013/0076458 A1 | 3/2013 | Katou et al. |
| 2013/0172441 A1 | 7/2013 | Takahata et al. |
| 2015/0111176 A1* | 4/2015 | Wachter ............. A61C 13/0013 433/180 |
| 2016/0184189 A1 | 6/2016 | Hagiwara et al. |
| 2017/0113411 A1 | 4/2017 | Watanabe et al. |

FOREIGN PATENT DOCUMENTS

| | | |
|---|---|---|
| CN | 105785714 A | 7/2016 |
| JP | 56-144478 A | 11/1981 |
| JP | 60-247515 A | 12/1985 |
| JP | 8-224790 A | 9/1996 |
| JP | 2000-24591 A | 1/2000 |
| JP | 2000-159621 A | 6/2000 |
| JP | 2005-314326 A | 11/2005 |
| JP | 2008-216875 * | 9/2008 |
| JP | 2008-216875 A | 9/2008 |
| JP | 2015-43793 A | 3/2015 |
| JP | 2017-81153 A | 5/2017 |
| WO | WO 2012/042911 A1 | 4/2012 |

OTHER PUBLICATIONS

Kaji et al, JP 2008-216875 Machine Translation, Sep. 18, 2008 (Year: 2008).*
International Search Report dated Dec. 19, 2017, in PCT/JP2017/037260 filed on Oct. 13, 2017.
Extended European Search Report dated May 18, 2020, in corresponding European Patent Application No. 17862364.1.

* cited by examiner

*Primary Examiner* — Jessica Whiteley
(74) *Attorney, Agent, or Firm* — Oblon, McClelland, Maier & Neustadt, L.L.P.

(57) ABSTRACT

The present invention provides a composition for optical three-dimensional modeling that offers desirable shape accuracy in optical three-dimensional modeling, and that provides desirable transparency and mechanical characteristics upon being cured. The present invention relates to a composition for optical three-dimensional modeling comprising a polymerizable monomer (a), an ultraviolet-absorbing inorganic particle (b), and a photopolymerization initiator (c).

12 Claims, No Drawings

COMPOSITION FOR OPTICAL THREE-DIMENSIONAL MODELING

TECHNICAL FIELD

The present invention relates to a composition for optical three-dimensional modeling, and to a method for producing a three-dimensional object with such a composition. More specifically, the present invention relates to a composition for optical three-dimensional modeling, particularly one suited as a dental material, that enables production of a three-dimensional object having excellent shape accuracy and transparency with desirable mechanical characteristics such as flexural strength and flexural modulus. The invention also relates to a method for optically producing a three-dimensional object using such a composition.

BACKGROUND ART

Patent Literature 1 discloses optical three-dimensional modeling, a method that produces a three-dimensional object through repeated exposure of controlled, necessary amounts of light energy to a liquid light-curable resin to cure the resin layer-by-layer as it is supplied onto the previously cured layer. Patent Literature 2 proposes a basic method for practical application of this technique, and, since its proposal, many other optical three-dimensional modeling techniques have been proposed.

In a typical method of producing a three-dimensional object by optical means, a computer-controlled ultraviolet laser is selectively applied to draw the desired pattern on the surface of a liquid light-curable resin composition placed in a vat. By being cured, the resin forms a layer of a predetermined thickness, and another cured layer is continuously formed on the cured layer by applying an ultraviolet laser to the liquid resin composition supplied onto the previously cured layer in an amount necessary to form a single layer. The layering process is repeated to produce a three-dimensional object of the desired shape. This technique has attracted great interest because it enables easy production of the desired three-dimensional object in a relatively short time period, even when the product has a very complex shape.

Three-dimensional objects created by stereolithography have expanded their use from simple concept models to wider applications such as test models and prototypes, and now require higher levels of shape accuracy than ever. Aside from such a property, these objects are also required to satisfy desirable mechanical characteristics. Particularly, stereolithography is expected to find use in the field of dental materials, which require high levels of shape accuracy (compatibility) to meet the demands of prosthetic appliances, or crowns or bridges as they are commonly called, which are produced in shapes that vary from patient to patient, aside from being complex in shape. Another issue is the inorganic particles typically added to improve product qualities such as strength. The properties of such inorganic particles are such that light easily passes or scatters through it, with the result that the product tends to suffer from poor shape accuracy.

Under these circumstances, various techniques have been proposed that enable optical three-dimensional modeling with good shape accuracy. For example, Patent Literature 3 proposes a resin composition for optical three-dimensional modeling containing an organic ultraviolet absorber. Patent Literature 4 describes an acrylic resin containing ultraviolet absorbable inorganic particles.

CITATION LIST

Patent Literature

Patent Literature 1: JP 56(1981)-144478 A
Patent Literature 2: JP 60(1985)-247515 A
Patent Literature 3: JP 8(1996)-224790 A
Patent Literature 4: JP 2000-24591 A

SUMMARY OF INVENTION

Technical Problem

Patent Literature 1 describing the resin composition for optical three-dimensional modeling is not specific as to its effectiveness in compositions that require addition of inorganic particles such as in dental materials. The acrylic resin of Patent Literature 2 is intended to improve durability against an organic ultraviolet absorber, and is not for light-curable materials or three-dimensional modeling. That is, Patent Literature 2 has no relevance to shape accuracy.

It is accordingly an object of the present invention to provide a composition for optical three-dimensional modeling that offers desirable shape accuracy in optical three-dimensional modeling, and that provides desirable transparency and mechanical characteristics upon being cured. The present invention is also intended to provide a composition for optical three-dimensional modeling, particularly one suited as a dental material, that offers desirable shape accuracy in optical three-dimensional modeling, and that provides desirable transparency and mechanical characteristics upon being cured.

Solution to Problem

Specifically, the present invention pertains to the following.

[1] A composition for optical three-dimensional modeling, comprising: a polymerizable monomer (a), an ultraviolet-absorbing inorganic particle (b), and a photopolymerization initiator (c).

[2] The composition for optical three-dimensional modeling according to item [1], wherein the composition further comprises an organic ultraviolet absorber (d).

[3] The composition for optical three-dimensional modeling according to item [2], wherein the organic ultraviolet absorber (d) comprises a benzotriazole compound.

[4] The composition for optical three-dimensional modeling according to any one of items [1] to [3], wherein the polymerizable monomer (a) comprises a (meth)acrylate polymerizable monomer and/or a (meth)acrylamide polymerizable monomer.

[5] The composition for optical three-dimensional modeling according to any one of items [1] to [4], wherein the polymerizable monomer (a) comprises an aliphatic difunctional (meth)acrylate polymerizable monomer, or an aromatic difunctional (meth)acrylate polymerizable monomer.

[6] The composition for optical three-dimensional modeling according to any one of items [1] to [5], wherein the polymerizable monomer (a) comprises a monofunctional (meth)acrylamide polymerizable monomer.

[7] The composition for optical three-dimensional modeling according to any one of items [1] to [6], wherein the ultraviolet-absorbing inorganic particle (b) comprises at least one ultraviolet-absorbable inorganic compound selected from the group consisting of zinc oxide, cerium oxide, europium oxide, and zirconium oxide.

[8] The composition for optical three-dimensional modeling according to any one of items [1] to [6], wherein the ultraviolet-absorbing inorganic particle (b) comprises zinc oxide and/or cerium oxide.

[9] The composition for optical three-dimensional modeling according to any one of items [1] to [8], wherein the ultraviolet-absorbing inorganic particle (b) has an average primary particle diameter of 500 nm or less.

[10] The composition for optical three-dimensional modeling according to any one of items [1] to [9], wherein the composition comprises the ultraviolet-absorbing inorganic particle (b) in an amount of 50 to 400 parts by mass relative to total 100 parts by mass of the polymerizable monomer (a).

[11] A dental material formed of a cured product of the composition for optical three-dimensional modeling of any one of items [1] to [10].

[12] A method for producing a three-dimensional object by optical three-dimensional modeling using the composition for optical three-dimensional modeling of any one of items [1] to [10].

Advantageous Effects of Invention

A composition for optical three-dimensional modeling of the present invention offers desirable shape accuracy in optical three-dimensional modeling, and provides desirable transparency and mechanical characteristics upon being cured. This makes the composition for optical three-dimensional modeling of the present invention suitable for use as a dental material (for example, a dental prosthetic appliance).

DESCRIPTION OF EMBODIMENTS

A composition for optical three-dimensional modeling of the present invention contains a polymerizable monomer (a), an ultraviolet-absorbing inorganic particle (b), and a photopolymerization initiator (c). In this specification, the upper and lower limits of numerical ranges (e.g., contents of components, and calculated values and various properties of components) may be combined as appropriate.

Polymerizable Monomer (a)

Preferred for use as the polymerizable monomer (a) used in the composition for optical three-dimensional modeling of the present invention are radically polymerizable monomers. Specific examples of radically polymerizable monomers as the polymerizable monomer (a) include (meth)acrylate polymerizable monomers; (meth)acrylamide polymerizable monomers; esters such as α-cyanoacrylic acid, α-halogenated acrylic acid, crotonic acid, cinnamic acid, sorbic acid, maleic acid, and itaconic acid; vinyl esters; vinyl ethers; mono-N-vinyl derivatives; and styrene derivatives. For curability, preferred as the polymerizable monomer (a) are (meth)acrylate polymerizable monomers, and (meth)acrylamide polymerizable monomers.

Monofunctional monomers having a single polymerizable group, and polyfunctional monomers having a plurality of polymerizable groups represent examples of the polymerizable monomer (a) of the present invention.

Examples of the monofunctional (meth)acrylate polymerizable monomers include 2-hydroxyethyl(meth)acrylate, 2-hydroxypropyl(meth)acrylate, 3-hydroxypropyl(meth) acrylate, 4-hydroxybutyl(meth)acrylate, 6-hydroxyhexyl (meth)acrylate, 10-hydroxydecyl(meth)acrylate, propylene glycol mono(meth)acrylate, glycerol mono(meth)acrylate, erythritol mono(meth)acrylate, methyl(meth)acrylate, ethyl (meth)acrylate, propyl(meth)acrylate, isopropyl(meth)acrylate, n-butyl(meth)acrylate, sec-butyl(meth)acrylate, t-butyl (meth)acrylate, isobutyl(meth)acrylate, n-hexyl(meth) acrylate, cyclohexyl(meth)acrylate, lauryl(meth)acrylate, cetyl(meth)acrylate, stearyl(meth)acrylate, isobornyl(meth) acrylate, benzyl(meth)acrylate, phenyl(meth)acrylate, 2,3-dibromopropyl(meth)acrylate, 3-(meth)acryloyloxypropyltrimethoxysilane, 11-(meth)acryloyloxyundecyltrimethoxysilane, and (meth)acrylamide. Examples of the monofunctional (meth)acrylamide polymerizable monomers include N-(meth)acryloylmorpholine, N,N-dimethyl(meth)acrylamide, N,N-diethyl (meth)acrylamide, N,N-di-n-propyl(meth)acrylamide, N,N-di-n-butyl(meth)acrylamide, N,N-di-n-hexyl(meth) acrylamide, N,N-di-n-octyl(meth)acrylamide, N,N-di-2-ethylhexyl(meth)acrylamide, N-hydroxyethyl(meth) acrylamide, and N,N-bis(2-hydroxyethyl)acrylamide. These may be used alone or in a combination of two or more. Preferred are (meth)acrylamide polymerizable monomers, particularly N-(meth)acryloylmorpholine, N,N-dimethyl (meth)acrylamide, and N,N-diethyl(meth)acrylamide for their desirable curability.

Examples of the polyfunctional monomers include aromatic difunctional polymerizable monomers, aliphatic difunctional polymerizable monomers, and tri- and higher-functional polymerizable monomers.

Examples of the aromatic difunctional polymerizable monomers include 2,2-bis((meth)acryloyloxyphenyl)propane, 2,2-bis[4-(3-acryloyloxy)-2-hydroxypropoxyphenyl] propane, 2,2-bis[4-(3-methacryloyloxy)-2-hydroxypropoxyphenyl]propane (commonly known as"Bis-GMA"), 2,2-bis(4-(meth)acryloyloxyethoxyphenyl)propane, 2,2-bis (4-(meth)acryloyloxypolyethoxyphenyl)propane, 2,2-bis(4-(meth)acryloyloxydiethoxyphenyl)propane, 2,2-bis(4-(meth)acryloyloxytetraethoxyphenyl)propane, 2,2-bis(4-(meth)acryloyloxypentaethoxyphenyl)propane, 2,2-bis(4-(meth)acryloyloxydipropoxyphenyl)propane, 2-(4-(meth) acryloyloxydiethoxyphenyl)-2-(4-(meth)acryloyloxyethoxyphenyl)propane, 2-(4-(meth)acryloyloxydiethoxyphenyl)-2-(4-(meth)acryloyloxytriethoxyphenyl)propane, 2-(4-(meth)acryloyloxydipropoxyphenyl)-2-(4-(meth)acryloyloxytriethoxyphenyl)propane, 2,2-bis(4-(meth)acryloyloxypropoxyphenyl)propane, 2,2-bis(4-(meth)acryloyloxyisopropoxyphenyl)propane, and 1,4-bis(2-(meth)acryloyloxyethyl)pyromellitate. These may be used alone or in a combination of two or more. Preferred are 2,2-bis[4-(3-methacryloyloxy)-2-hydroxypropoxyphenyl] propane (commonly known as "Bis-GMA"), and 2,2-bis(4-(meth)acryloyloxypolyethoxyphenyl)propane because these offer desirable curability, and desirable strength in the cured product. Preferred as the 2,2-bis(4-(meth)acryloyloxypolyethoxyphenyl)propane is 2,2-bis(4-methacryloyloxypolyethoxyphenyl)propane (a compound in which the average number of moles of ethoxy groups added is 2.6; commonly known as "D-2.6E").

Examples of the aliphatic difunctional polymerizable monomers include glycerol di(meth)acrylate, ethylene glycol di(meth)acrylate, diethylene glycol di(meth)acrylate, triethylene glycol di(meth)acrylate, propylene glycol di(meth) acrylate, butylene glycol di(meth)acrylate, neopentyl glycol di(meth)acrylate, polyethylene glycol di(meth)acrylate, 1,3-butanediol di(meth)acrylate, 1,4-butanediol di(meth)acrylate, 1,6-hexanediol di(meth)acrylate, 2-ethyl-1,6-hexanediol di(meth)acrylate, 1,9-nonanediol di(meth)acrylate, 1,10-decanediol di(meth)acrylate, 1,2-bis(3-methacryloxy-2-hydroxypropoxy)ethane, and 2,2,4-trimethylhexamethylene-bis(2-carbamoyloxyethyl)dimethacrylate (commonly known as "UDMA"). Preferred is 2,2,4-trimethylhexamethylene-bis(2-carbamoyloxyethyl) dimethacrylate because it offers desirable curability, and desirable strength in the cured product. These may be used alone or in a combination of two or more.

Examples of the tri- and higher-functional polymerizable monomers include trimethylolpropane tri(meth)acrylate, trimethylolethane tri(meth)acrylate, trimethylol methane tri(meth)acrylate, pentaerythritol tri(meth)acrylate, pentaerythritol tetra(meth)acrylate, dipentaerythritol penta(meth)acrylate, N,N-(2,2,4-trimethylhexamethylene)bis[2-(aminocarboxy)propane-1,3-thol]tetra(meth)acrylate, and 1,7-diacryloyloxy-2,2,6,6-tetra(meth)acryloyloxymethyl-4-oxyheptane. Preferred are N,N-(2,2,4-trimethylhexamethylene)bis[2-(aminocarboxy)propane-1,3-diol]tetramethacrylate, and 1,7-diacryloyloxy-2,2,6,6-tetraacryloyloxymethyl-4-oxyheptane because these offer desirable curability, and desirable strength in the cured product.

When the polymerizable monomer (a) contains an aliphatic difunctional (meth)acrylate polymerizable monomer or an aromatic difunctional (meth)acrylate polymerizable monomer, the content of the difunctional (meth)acrylate polymerizable monomer is preferably 50 to 100 parts by mass, more preferably 50 to 90 parts by mass, further preferably 55 to 85 parts by mass relative to total 100 parts by mass of the polymerizable monomer (a). When the polymerizable monomer (a) contains a monofunctional (meth)acrylate polymerizable monomer, the content of the monofunctional (meth)acrylate polymerizable monomer is preferably 10 to 55 parts by mass, more preferably 10 to 50 parts by mass, further preferably 15 to 45 parts by mass relative to total 100 parts by mass of the polymerizable monomer (a). As used herein, "content of a polymerizable monomer relative to total 100 parts by mass of the polymerizable monomer components" means the content of the polymerizable monomer (in mass %) of when the total amount of the polymerizable monomer components is converted to 100 mass %. Accordingly, the total amount of the polymerizable monomer components does not exceed 100 parts by mass. The content of the polymerizable monomer (a) is preferably 15 to 75 mass %, more preferably 20 to 70 mass %, further preferably 25 to 68 mass % relative to the composition for optical three-dimensional modeling as a whole.

Ultraviolet-Absorbing Inorganic Particle (b)

The inorganic particle (b) having ultraviolet absorbability (hereinafter, also referred to as "ultraviolet-absorbing inorganic particle (b)") is preferably an inorganic particle containing at least one ultraviolet-absorbable inorganic compound selected from the group consisting of zinc oxide, cerium oxide, europium oxide, zirconium oxide, and titanium oxide, more preferably an inorganic particle containing at least one ultraviolet-absorbable inorganic compound selected from the group consisting of zinc oxide, cerium oxide, europium oxide, and zirconium oxide. The ultraviolet-absorbing inorganic particle (b) may be a composite of the ultraviolet-absorbable inorganic compound and an inorganic compound having no ultraviolet absorbability. The content of the ultraviolet-absorbable inorganic compound in the ultraviolet-absorbing inorganic particle (b) is preferably 50 mass % or more, more preferably 70 mass % or more, further preferably 80 mass % or more, particularly preferably 90 mass % or more, though the content is not particularly limited as long as the ultraviolet-absorbable inorganic compound is contained as a main component. The content of the ultraviolet-absorbable inorganic compound in the ultraviolet-absorbing inorganic particle (b) may be 100 mass %. The ultraviolet-absorbable inorganic compounds may be used alone or in a combination of two or more. Particularly preferred are zinc oxide and/or cerium oxide for their desirable transparency.

Examples of the inorganic compound having no ultraviolet absorbability include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. The form of the composite is not particularly limited, and the composite may be in the form of a melted mixture of two inorganic compounds; an inorganic compound (for example, an inorganic compound with no ultraviolet absorbability) coated over the particle surface of another inorganic compound (for example, the ultraviolet-absorbable inorganic compound); an inorganic compound (for example, an inorganic compound with no ultraviolet absorbability) layered over the particle surface of another inorganic compound (for example, the ultraviolet-absorbable inorganic compound) in a core-in-shell structure; or a cluster of two inorganic compounds.

For ensured transparency, the ultraviolet-absorbing inorganic particle (b) has an average primary particle diameter of preferably 500 nm or less, more preferably 1 nm to 500 nm, further preferably 5 nm to 400 nm, particularly preferably 10 nm to 300 nm, most preferably 15 nm to 200 nm.

In this specification, the average primary particle diameter of the inorganic particles can be determined by light microscopy or electron microscopy. Specifically, it is convenient to use a light microscope for the measurement of particles having a particle diameter of 100 nm or more, and an electron microscope for the measurement of particles having a particle diameter of less than 100 nm.

In light microscopy or electron microscopy, for example, particles may be photographed with a scanning electron microscope (Model S-4000; Hitachi), and the size of particles (at least 200 particles) observed in a unit field of the micrograph may be measured using image-analyzing particle-size-distribution measurement software (Macview available from Mountech Co., Ltd.). Here, the particle diameter is determined as an arithmetic mean value of the maximum and minimum lengths of particles, and the average primary particle diameter is calculated from the number of particles and the particle diameter.

The content of the ultraviolet-absorbing inorganic particle (b) in the composition for optical three-dimensional modeling of the present invention is not particularly limited. However, from the viewpoints of properties such as the viscosity of the composition for optical three-dimensional modeling, and the shape accuracy of the cured product, the content of the ultraviolet-absorbing inorganic particle (b) is preferably 10 to 500 parts by mass relative to total 100 parts by mass of the polymerizable monomer (a). The content of the ultraviolet-absorbing inorganic particle (b) is more preferably 20 parts by mass or more, further preferably 30 parts by mass or more, particularly preferably 40 parts by mass or more, most preferably 50 parts by mass or more relative to total 100 parts by mass of the polymerizable monomer (a).

The product may fail to satisfy the desired shape accuracy when the content of the ultraviolet-absorbing inorganic particle (b) is less than 10 parts by mass relative to total 100 parts by mass of the polymerizable monomer (a). When the content of the ultraviolet-absorbing inorganic particle (b) is more than 500 parts by mass relative to total 100 parts by mass of the polymerizable monomer (a), the composition for optical three-dimensional modeling may increase its viscosity, and may fail to form a product. The content of the ultraviolet-absorbing inorganic particle (b) is more preferably 400 parts by mass or less, further preferably 300 parts by mass or less relative to total 100 parts by mass of the polymerizable monomer (a). The content of the ultraviolet-absorbing inorganic particle (b) is preferably 20 to 80 mass %, more preferably 25 to 75 mass %, further preferably 30 to 72 mass %, particularly preferably 31 to 72 mass % of the composition for optical three-dimensional modeling as a whole.

For the purpose of adjusting the miscibility of the ultraviolet-absorbing inorganic particle (b) with the polymerizable monomer (a), the ultraviolet-absorbing inorganic particle (b) may be subjected to a surface treatment in advance, as required, using known surface treatment agents such as acidic group-containing organic compounds; fatty acid amides such as saturated fatty acid amides, unsaturated fatty acid amides, saturated fatty acid bisamides, and unsaturated fatty acid bisamides; and organometallic compounds such as silane coupling agents (organosilicon compounds), organic titanium compounds, organic zirconium compounds, and organic aluminum compounds. The acidic group-containing organic compounds are preferred for improving the mechanical strength of the cured product through improved chemical bonding between the polymerizable monomer (a) and the ultraviolet-absorbing inorganic particle (b). Examples of the acidic group-containing organic compounds include acidic group-containing organic compounds having at least one acidic group, for example, such as a phosphoric acid group, a pyrophosphoric acid group, a thiophosphoric acid group, a phosphonic acid group, a sulfonic acid group, and a carboxylic acid group. The acidic group-containing organic compounds are preferably phosphoric acid group-containing organic compounds having at least one phosphoric acid group. When using two or more surface treatment agents, the surface treatment layer may be a mixture of two or more surface treatment agents, or may be a laminate of more than one layer of surface treatment agent.

Examples of the acidic group-containing organic compounds having a phosphoric acid group include 2-ethylhexyl acid phosphate, stearyl acid phosphate, 2-(meth)acryloyloxyethyl dihydrogen phosphate, 3-(meth)acryloyloxypropyl dihydrogen phosphate, 4-(meth)acryloyloxybutyl dihydrogen phosphate, 5-(meth)acryloyloxypentyl dihydrogen phosphate, 6-(meth)acryloyloxyhexyl dihydrogen phosphate, 7-(meth)acryloyloxyheptyl dihydrogen phosphate, 8-(meth)acryloyloxyoctyl dihydrogen phosphate, 9-(meth)acryloyloxynonyl dihydrogen phosphate, 10-(meth)acryloyloxydecyl dihydrogen phosphate, 11-(meth)acryloyloxyundecyl dihydrogen phosphate, 12-(meth)acryloyloxydodecyl dihydrogen phosphate, 16-(meth)acryloyloxyhexadecyl dihydrogen phosphate, 20-(meth)acryloyloxyicosyl dihydrogen phosphate, bis[2-(meth)acryloyloxyethyl]hydrogen phosphate, bis[4-(meth)acryloyloxybutyl]hydrogen phosphate, bis[6-(meth)acryloyloxyhexyl]hydrogen phosphate, bis[8-(meth)acryloyloxyoctyl]hydrogen phosphate, bis[9-(meth)acryloyloxynonyl]hydrogen phosphate, bis[10-(meth)acryloyloxydecyl]hydrogen phosphate, 1,3-di(meth) acryloyloxypropyl dihydrogen phosphate, 2-(meth)acryloyloxyethylphenyl hydrogen phosphate, 2-(meth)acryloyloxyethyl-2-bromoethyl hydrogen phosphate, bis[2-(meth)acryloyloxy-(1-hydroxymethyl)ethyl]hydrogen phosphate, and acid chlorides, alkali metal salts, and ammonium salts thereof.

The acidic group-containing organic compounds having an acidic group such as a pyrophosphoric acid group, a thiophosphoric acid group, a phosphonic acid group, a sulfonic acid group, and a carboxylic acid group may preferably be those recited in, for example, WO2012/042911.

Examples of the saturated fatty acid amides include palmitamide, stearamide, and behenamide. Examples of the unsaturated fatty acid amides include oleamide and erucamide. Examples of the saturated fatty acid bisamides include ethylenebispalmitamide, ethylenebisstearamide, and hexamethylenebisstearamide. Examples of the unsaturated fatty acid bisamides include ethylenebisoleamide, hexamethylenebisoleamide, and N,N'-dioleylsebacamide.

Examples of the organosilicon compounds include compounds represented by $R^1{}_n SiX_{4-n}$ (wherein $R^1$ is a substituted or unsubstituted hydrocarbon group of 1 to 12 carbon atoms, X is a C1 to C4 alkoxy group, a hydroxyl group, a halogen atom, or a hydrogen atom, and n is an integer of 0 to 3, where $R^1$ may be the same or different when a plurality of $R^1$ exists, and X may be the same or different when a plurality of X exists).

Specific examples include methyltrimethoxysilane, dimethyldimethoxysilane, phenyltrimethoxysilane, diphenyldimethoxysilane, methyltriethoxysilane, dimethyldiethoxysilane, phenyltriethoxysilane, diphenyldiethoxysilane, isobutyltrimethoxysilane, vinyltrimethoxysilane, vinyltriethoxysilane, vinyl tris(β-methoxyethoxy)silane, 3,3,3-trifluoropropyltrimethoxysilane, methyl-3,3,3-trifluoropropyldimethoxysilane, β-(3,4-epoxycyclohexyl)ethyltrimethoxysilane, γ-glycidoxypropyltrimethoxysilane, γ-glycidoxypropylmethyldiethoxysilane, γ-glycidoxypropyltriethoxysilane, γ-methacryloyloxypropylmethyldimethoxysilane, γ-methacryloyloxypropylmethyldiethoxysilane, N-β-(aminoethyl)-γ-aminopropylmethyldimethoxysilane, N-β-(aminoethyl)-γ-aminopropyltrimethoxysilane, N-β-(aminoethyl)-γ-aminopropyltriethoxysilane, γ-aminopropyltrimethoxysilane, γ-aminopropyltriethoxysilane, N-phenyl-γ-aminopropyltrimethoxysilane, γ-mercaptopropyltrimethoxysilane, trimethylsilanol, methyltrichlorosilane, methyldichlorosilane, dimethyldichlorosilane, trimethylchlorosilane, phenyltrichlorosilane, diphenyklichlorosilane, vinyltrichlorosilane, trimethylbromosilane, diethylsilane, vinyltriacetoxysilane, ω-(meth)acryloyloxyalkyltrimethoxysilane [3 to 12 carbon atoms between the (meth)acryloyloxy group and the silicon atom; e.g., γ-methacryloyloxypropyltrimethoxysilane], and ω-(meth)acryloyloxyalkyltriethoxysilane [3 to 12 carbon atoms between the (meth)acryloyloxy group and the silicon atom; e.g., γ-methacryloyloxypropyltriethoxysilane]. As used herein, "(meth)acryloyloxy" is intended to include both methacryloyloxy and acryloyloxy.

Preferred are coupling agents having a functional group that is copolymerizable with the polymerizable monomer. Examples of such coupling agents include ω-(meth)acryloyloxyalkyltrimethoxysilane [3 to 12 carbon atoms between the (meth)acryloyloxy group and the silicon atom], ω-(meth)acryloyloxyalkyltriethoxysilane [3 to 12 carbon atoms between the (meth)acryloyloxy group and the silicon atom], vinyltrimethoxysilane, vinyltriethoxysilane, vinyltriacetoxysilane, and γ-glycidoxypropyltrimethoxysilane.

Examples of the organic titanium compounds include tetramethyl titanate, tetraisopropyl titanate, tetra n-butyl titanate, butyl titanate dimers, and tetra(2-ethylhexyl)titanate.

Examples of the organic zirconium compounds include zirconium isopropoxide, zirconium n-butoxide, zirconium acetylacetonate, and zirconyl acetate.

Examples of the organic aluminum compounds include aluminum acetylacetonate, aluminum organic acid salt chelate compounds.

The surface treatment may be carried out using a known method, and the method is not particularly limited For example, the surface treatment agent may be added by being sprayed into the inorganic filler being vigorously stirred, or the surface treatment agent may be dispersed or dissolved in a suitable solvent with the inorganic filler, and the solvent may be removed.

The amount of surface treatment agent is not particularly limited. For example, the surface treatment agent is preferably 0.1 to 50 parts by mass relative to 100 parts by mass of the ultraviolet-absorbing inorganic particle (b).

Photopolymerization Initiator (c)

The photopolymerization initiator (c) used in the present invention may be one selected from polymerization initiators commonly used in industry. Preferably, the photopolymerization initiator (c) is a photopolymerization initiator used for dental applications.

Examples of the photopolymerization initiator (c) include (bis)acylphosphine oxides, thioxanthones or quaternary ammonium salts of thioxanthones, ketals, α-diketones, coumalins, anthraquinones, benzoin alkyl ether compounds, and α-aminoketone compounds.

Preferred for use as the photopolymerization initiator (c) is at least one selected from the group consisting of (bis) acylphosphine oxides and salts thereof, and α-diketones. In this way, a composition for optical three-dimensional modeling can be obtained that has desirable photocurability both in the ultraviolet and visible regions, and that shows sufficient photocurability even when the light source is a laser such as an Ar laser and a He—Cd laser, or a lighting such as a halogen lamp, a xenon lamp, a metal halide lamp, a light emitting diode (LED), a mercury lamp, and a fluorescent lamp.

Examples of the (bis)acylphosphine oxides include acylphosphine oxides such as 2,4,6-trimethylbenzoyldiphenylphosphine oxide, 2,6-dimethoxybenzoyldiphenylphosphine oxide, 2,6-dichlorobenzoyldiphenylphosphine oxide, 2,4,6-trimethylbenzoylmethoxyphenylphosphine oxide, 2,4,6-trimethylbenzoylethoxyphenylphosphine oxide, 2,3,5,6-tetramethylbenzoykliphenylphosphine oxide, benzoyl di-(2,6-dimethylphenyl)phosphonate, sodium salts of 2,4,6-trimethylbenzoylphenylphosphine oxide, potassium salts of 2,4,6-trimethylbenzoyldiphenylphosphine oxide, and ammonium salts of 2,4,6-trimethylbenzoyldiphenylphosphine oxide. Examples of the bisacylphosphine oxides include bis(2,6-dichlorobenzoyl)phenylphosphine oxide, bis (2,6-dichlorobenzoyl)-2,5-dimethylphenylphosphine oxide, bis(2,6-dichlorobenzoyl)-4-propylphenylphosphine oxide, bis(2,6-dichlorobenzoyl)-1-naphthylphosphine oxide, bis(2,6-dimethoxybenzoyl)phenylphosphine oxide, bis(2,6-dimethoxybenzoyl)-2,4,4-trimethylpentylphosphine oxide, bis(2,6-dimethoxybenzoyl)-2,5-dimethylphenylphosphine oxide, bis(2,4,6-trimethylbenzoyl)phenylphosphine oxide, and bis (2,5,6-trimethylbenzoyl)-2,4,4-trimethylpentylphosphine oxide. The compounds recited in JP 2000-159621 A also may be used.

Among these (bis)acylphosphine oxides, particularly preferred as the photopolymerization initiator (c) are 2,4,6-trimethylbenzoyldiphenylphosphine oxide, 2,4,6-trimethylbenzoylmethoxyphenylphosphine oxide, bis(2,4,6-trimethylbenzoyl)phenylphosphine oxide, and sodium salts of 2,4,6-trimethylbenzoylphenylphosphine oxide.

Examples of the α-diketones include diacetyl, benzyl, camphorquinone, 2,3-pentadione, 2,3-octadione, 9,10-phenanthrenequinone, 4,4'-oxybenzyl, and acenaphthenequinone. Camphorquinone is particularly preferred when the light source emits light in the visible region.

The content of the photopolymerization initiator (c) in the composition for optical three-dimensional modeling of the present invention is not particularly limited. However, from the viewpoint of the curability and other properties of the composition for optical three-dimensional modeling, the content of the photopolymerization initiator (c) is preferably 0.01 to 10 parts by mass relative to total 100 parts by mass of the polymerizable monomer (a). When the content of the photopolymerization initiator (c) is less than 0.01 parts by mass relative to total 100 parts by mass of the polymerizable monomer (a), the composition for optical three-dimensional modeling may fail to sufficiently cure, with the result that the product may not be obtained as intended. The content of the photopolymerization initiator (c) is more preferably 0.05 parts by mass or more, further preferably 0.1 parts by mass or more relative to total 100 parts by mass of the polymerizable monomer (a). When the content of the photopolymerization initiator (c) is more than 10 parts by mass relative to total 100 parts by mass of the polymerizable monomer (a), the photopolymerization initiator (c) may precipitate from the composition for optical three-dimensional modeling when the solubility of the photopolymerization initiator itself is low. The content of the photopolymerization initiator (c) is more preferably 7.5 parts by mass or less, further preferably 5 parts by mass or less relative to total 100 parts by mass of the polymerizable monomer (a).

Organic Ultraviolet Absorber (d)

For improved shape accuracy, the composition for optical three-dimensional modeling of the present invention may use an organic ultraviolet absorber (d).

Examples of the organic ultraviolet absorber (d) include benzotriazole compounds such as 2-(2-hydroxy-5-methylphenyl)benzotriazole (TINUVIN P), 2-(2-hydroxy-5-tert-octylphenyl)benzotriazole (TINUVIN 329), 2-(2'-hydroxy-3',5'-di-tert-butylphenyl)benzotriazole, 2-(2'-hydroxy-5'-tert-butylphenyl)benzotriazole, 2-(2'-hydroxy-3'-tert-butyl-5'-methylphenyl)benzotriazole, 2-[2'-hydroxy-3'-butyl-5'-(2"-carboxyoctyl-ethyl)phenyl]benzotriazole, 2-(2'-hydroxy-3',5'-di-tert-amylphenyl)benzotriazole, 2-(2'-hydroxy-3'-tert-butyl-5'-methylphenyl)benzotriazole, 2-(2'-hydroxy-3'-tert-butyl-5'-methylphenyl)-5-chlorobenzotriazole, and 2-(2'-hydroxy-3',5'-di-tert-butylphenyl)-5-chlorobenzotriazole; benzophenone compounds such as 2,4-dihydroxybenzophenone, 2-hydroxy-4-methoxybenzophenone, 2-hydroxy-4-n-octoxybenzophenone, 2-hydroxy-4-(dodecyloxy)benzophenone, 2-hydroxy-4-(octadecyloxy)benzophenone, 2,2'-dihydroxy-4-methoxybenzophenone, and 2,2'-dihydroxy-4,4'-dimethoxybenzophenone; and thiophene compounds such as 2,5-bis(5-t-butyl-2-benzooxazolynthiophene. Preferred for desirable shape accuracy are benzotriazole compounds, more preferably benzotriazole compounds containing a hydroxyl group attached at position 2 of the aromatic ring bound to a nitrogen atom of the triazole structure, further preferably benzotriazole compounds containing a hydroxyl group attached at position 2 of the aromatic ring bound to a nitrogen atom of the triazole structure, and having a C1 to C12 alkyl group at position 3 and/or 5 of the aromatic ring.

The organic ultraviolet absorber (d) may be any one of these and other compounds used alone, or may be two or more of these and other compounds used in combination. The content of the organic ultraviolet absorber (d) is preferably in a range of 0.001 to 10 parts by mass, more preferably 0.01 to 5 parts by mass relative to 100 parts by mass of the polymerizable monomer (a).

The composition for optical three-dimensional modeling of the present invention is not particularly limited, as long as it contains the polymerizable monomer (a), the ultraviolet-absorbing inorganic particle (b), and the photopolymerization initiator (c). For example, the composition for optical three-dimensional modeling of the present invention may contain other components, in addition to these components. The composition for optical three-dimensional modeling of the present invention may be produced following a known method. The content of the other components in the composition for optical three-dimensional modeling may be less than 10 mass %, less than 5.0 mass %, or less than 1.0 mass %.

The composition for optical three-dimensional modeling of the present invention may contain a polymerization accelerator to improve photocurability, provided that addition of a polymerization accelerator is not against the gist of the present invention. Examples of such polymerization accelerators include 4-(N,N-dimethylamino)ethyl benzoate, 4-(N,N-dimethylamino)methyl benzoate, 4-(N,N-dimethylamino)-n-butoxyethyl benzoate, 4-N,N-dimethylamino-2-(methacryloyloxy)ethyl benzoate, 4-(N,N-dimethylamino) benzophenone, and 4-(N,N-dimethylamino)butyl benzoate. Preferred for imparting desirable curability to the composition for optical three-dimensional modeling is at least one selected from the group consisting of 4-(N,N-dimethylamino)ethyl benzoate, 4-(N,N-dimethylamino)-n-butoxyethyl benzoate, and 4-(N,N-dimethylamino)benzophenone.

The composition for optical three-dimensional modeling of the present invention may further contain particles other than the ultraviolet-absorbing inorganic particle (b), in order to adjust the paste characteristics, or to improve the mechanical strength of the cured product of the composition for optical three-dimensional modeling. Examples of such other particles include organic particles, inorganic particles, and organic-inorganic composite particles. These particles may be used either alone or in a combination of two or more.

Examples of the materials of the organic particles include polymethyl methacrylate, polyethyl methacrylate, a methyl methacrylate-ethyl methacrylate copolymer, crosslinked polymethyl methacrylate, crosslinked polyethyl methacrylate, polyesters, polyamides, polycarbonates, polyphenylene ethers, polyoxymethylene, polyvinyl chloride, polystyrene, polyethylene, polypropylene, chloroprene rubber, nitrile rubber, an ethylene-vinyl acetate copolymer, a styrene-butadiene copolymer, an acrylonitrile-styrene copolymer, and an acrylonitrile-styrene-butadiene copolymer. These may be used either alone or in a combination of two or more. The organic particle is not limited to a particular shape, and may be one appropriately selected from particles of different diameters. Preferred for shape accuracy is an organic particle having an average particle diameter of 1.0 μm or less.

Examples of the materials of the inorganic particles include quartz, silica, alumina, silica-titania, silica-titania-barium oxide, silica-zirconia, silica-alumina, lanthanum glass, borosilicate glass, soda glass, barium glass, strontium glass, glass ceramic, aluminosilicate glass, barium boroaluminosilicate glass, strontium boroaluminosilicate glass, fluoroaluminosilicate glass, calcium fluoroaluminosilicate glass, strontium fluoroaluminosilicate glass, barium fluoroaluminosilicate glass, and strontium calcium fluoroaluminosilicate glass. These may be used either alone or in a combination of two or more. The inorganic filler is not limited to a particular shape, and may be one appropriately selected from fillers of different shapes, such as irregular fillers, and spherical fillers. Preferred for shape accuracy and transparency is an inorganic particle having an average particle diameter of 1.0 μm or less.

The composition for optical three-dimensional modeling of the present invention may contain a known stabilizer, in order to inhibit deterioration, or to adjust photocurability. Examples of such stabilizers include polymerization inhibitors, and antioxidants.

Examples of the polymerization inhibitors include hydroquinone, hydroquinone monomethyl ether, dibutylhydroquinone, dibutylhydroquinone monomethyl ether, t-butyl catechol, 2-t-butyl-4,6-dimethylphenol, 2,6-di-t-butylphenol, and 3,5-di-t-butyl-4-hydroxytoluene. The polymerization inhibitor content is preferably 0.001 to 1.0 parts by mass relative to total 100 parts by mass of the polymerizable monomer (a).

The composition for optical three-dimensional modeling of the present invention may contain a known additive, in order to adjust color or paste characteristics. Examples of such additives include pigments, dyes, organic solvents, and thickeners.

A certain embodiment (X-1) of the present invention is a composition for optical three-dimensional modeling containing the polymerizable monomer (a), the ultraviolet-absorbing inorganic particle (b), and the photopolymerization initiator (c), and in which the ultraviolet-absorbing inorganic particle (b) contains titanium oxide. In another embodiment (X-2), the composition for optical three-dimensional modeling of embodiment (X-1) contains an aliphatic difunctional (meth)acrylate polymerizable monomer, or an aromatic difunctional (meth)acrylate polymerizable monomer. In another embodiment (X-3), the polymerizable monomer (a) in the composition for optical three-dimensional modeling of embodiment (X-1) or (X-2) contains a monofunctional (meth)acrylamide polymerizable monomer. In another embodiment (X-4), the composition for optical three-dimensional modeling of any one of embodiments (X-1) to (X-3) further contains the organic ultraviolet absorber (d). In another embodiment (X-5), the organic ultraviolet absorber (d) in embodiment (X-4) contains a benzotriazole compound. In another embodiment (X-6), the ultraviolet-absorbing inorganic particle (b) in any one of embodiments (X-1) to (X-5) has an average primary particle diameter of 500 nm or less. In another embodiment (X-7), the ultraviolet-absorbing inorganic particle (b) in any one of embodiments (X-1) to (X-6) is contained in an amount of 50 to 400 parts by mass relative to total 100 parts by mass of the polymerizable monomer (a). In these embodiments, the amounts of the components may be appropriately varied, and various changes may be made to the embodiments, including addition and deletion of any of the components, following the foregoing descriptions. In the foregoing embodiments, the makeup and the properties (e.g., shape accuracy, transparency (ΔL)) of the compositions may be appropriately changed to have different values, and these may be combined.

The composition for optical three-dimensional modeling of the present invention has desirable shape accuracy, and the cured product has desirable transparency and mechanical characteristics. Accordingly, the composition for optical three-dimensional modeling of the present invention can be used in applications where such advantages can be exploited. As an example, the composition for optical three-dimensional modeling of the present invention is applicable to optical three-dimensional modeling of a three-dimensional object; dental materials; cast molding or injection molding of various products such as film-shaped objects and other molded products; and dies for coating and vacuum molding. The composition for optical three-dimensional modeling of the present invention is particularly suited as a dental material.

Another embodiment of the present invention is a method that produces a three-dimensional object by optical three-dimensional modeling using any of the compositions for optical three-dimensional modeling above.

In optical three-dimensional modeling using the composition for optical three-dimensional modeling of the present invention, any known method and device for optical three-dimensional modeling may be used. In the present invention, the light energy used to cure the resin is preferably an active energy beam. As used herein, "active energy beam" means an energy ray capable of curing a light-curable resin composition, and includes, for example, ultraviolet light, an electron beam, X-rays, radiant rays, and high-frequency waves. For example, the active energy beam may be ultraviolet light of 300 to 400 nm wavelengths. The light source of active energy beam may be, for example, a laser such as an Ar laser, and a He—Cd laser; or a lighting such as a halogen lamp, a xenon lamp, a metal halide lamp, an LED, a mercury lamp, and a fluorescent lamp. Lasers are particularly preferred. When the light source is a laser, the fabrication time can be reduced by increasing the energy level, and a highly accurate three-dimensional object can be obtained by taking advantage of the desirable convergence of a laser beam.

Optical three-dimensional modeling using the composition for optical three-dimensional modeling of the present invention may use any known method and any known stereolithography system, and the method and device are not particularly limited, as mentioned above. However, a typical example of the optical three-dimensional modeling preferred for use in the present invention is a method that produces a three-dimensionally object of the desired shape through a repeated procedure that includes: a step of forming a cured layer by selectively applying an active energy beam to the composition for optical three-dimensional modeling to obtain a cured layer having a desired pattern, and a step of continuously forming another cured layer by applying an active energy beam in a similar fashion to the uncured, liquid composition for optical three-dimensional modeling supplied onto the previously cured layer. The resulting three-dimensional object may be used as it is, or after improving mechanical characteristics, shape stability, or other properties by post-curing the product under applied light or heat.

The three-dimensional object obtained by optical three-dimensional modeling is not limited to a particular structure, shape, or size, and these may be selected according to use. Typical examples of areas to which the optical three-dimensional modeling of the present invention is applicable include production of various models and molds, including, for example, models for assessing external designs in a designing process; models for checking functions of components and parts; resin molds for making molds; base models for making dies; and direct molds for prototype dies. More specifically, the optical three-dimensional modeling of the present invention is applicable to, for example, production of models or work models for precision components and parts, electrical and electronic components, furniture, architectural structures, automobile parts, various containers and vessels, castings, dies, and matrices. Because the cured product has desirable transparency and mechanical strength, the optical three-dimensional modeling of the present invention is particularly effective in applications such as dental prosthetic appliances, including coronal restoration materials such as crowns and bridges.

Alternative forms of the present invention include different combinations of the configurations described above to such an extent that such combinations are made within the technical scope of the present invention, provided that the effects of the present invention are obtained.

EXAMPLES

The following describes the present invention in greater detail by way of Examples. It is to be noted, however, that the present invention is in no way limited by the following Examples, and various changes may be made by a person of ordinary skill in the art within the technical idea of the present invention. The components used for the compositions for optical three-dimensional modeling of Examples and Comparative Example are as laid out below with the abbreviations used.

Polymerizable Monomer (a)
UDMA: 2,2,4-Trimethylhexamethylene-bis(2-carbamoyloxyethyl)dimethacrylate (Shin-Nakamura Chemical Co., Ltd.)
D-2.6E: 2,2-Bis(4-methacryloyloxypolyethoxyphenyl)propane (Shin-Nakamura Chemical Co., Ltd.)
TEGDMA: Triethylene glycol dimethacrylate (Shin-Nakamura Chemical Co., Ltd.)
ACMO: N-Acryloylmorpholine (KJ Chemicals Corporation)
Ultraviolet-Absorbing Inorganic Particle (b)
Inorganic particles (b)-1 to (b)-3 are obtained using the following procedures.
Inorganic particle (b)-1: Zinc Oxide Powder Treated with 10-Methacryloyloxydecyl Dihydrogen Phosphate
For preparation, 100 g of zinc oxide (NANOFINE-50 available from Sakai Chemical Industry Co., Ltd.), 0.5 g of 10-methacryloyloxydecyl dihydrogen phosphate (available from Toho Chemical Industry Co., Ltd.), and 200 mL of toluene were charged into a 500-mL one-neck eggplant flask, and the mixture was stirred at room temperature for 2 hours. After removing toluene under reduced pressure, the mixture was vacuum dried at 40° C. for 16 hours, and at 90° C. for 3 hours to obtain a zinc oxide powder surface-treated with 10-methacryloyloxydecyl dihydrogen phosphate [inorganic particle (b)-1]. The inorganic particle (b)-1 was photographed with a scanning electron microscope (Model S-4000; Hitachi), and the size of particles (at least 200 particles) observed in a unit field of the micrograph was measured using image-analyzing particle-size-distribution measurement software (Macview available from Mountech Co., Ltd.). The particles had an average primary particle diameter of 25 nm.

Inorganic Particle (b)-2: Silica-Alumina-Coated Zinc Oxide Powder Treated with 10-Methacryloyloxydecyl Dihydrogen Phosphate
A silica-alumina-coated zinc oxide powder surface-treated with 10-methacryloyloxydecyl dihydrogen phosphate was obtained in the same manner as for the inorganic particle (b)-1, except that silica-alumina-coated zinc oxide (NANOFINE-50A available from Sakai Chemical Industry Co., Ltd.) was used as inorganic particles. The silica-alumina-coated zinc oxide powder had an average primary particle diameter of 30 nm.

Inorganic Particle (b)-3: Cerium Oxide Powder Treated with 10-Methacryloyloxydecyl Dihydrogen Phosphate A cerium oxide powder surface-treated with 10-methacryloyloxydecyl dihydrogen phosphate was obtained in the same manner as for the inorganic particle (b)-1, except that cerium oxide (Ceriguard (W-500) available from Daito Kasei) was used as inorganic particles. The cerium oxide powder had an average primary particle diameter of 35 nm.

Photopolymerization Initiator (c)

TPO: 2,4,6-Trimethylbenzoyldiphenylphosphine oxide

Organic Ultraviolet Absorber (d)

HOB: 2-(2-Hydroxy-5-tert-octylphenyl)benzotriazole

Polymerization Inhibitor

BHT: 3,5-Di-t-butyl-4-hydroxytoluene

The components were mixed in the amounts shown in Tables 1 and 2 under ordinary temperature (20° C.±15° C., JIS (Japan Industrial Standards) Z 8703:1983) to prepare pastes as compositions for optical three-dimensional modeling of Examples 1 to 9 and Comparative Example 1.

Shape Accuracy

The compositions of Examples and Comparative Example shown in Tables 1 and 2 were used to prepare three-dimensional cube-shaped objects measuring 10.0 mm each side, using a stereolithography device (DigitalWax® 028J-Plus available from DWS). The object was washed with methanol, and was measured for dimensions (unit: mm) using a micrometer after removing unpolymerized monomers. Shape accuracy was calculated using the following formula. As a rule, the object prepared in this fashion shows desirable shape accuracy, and a dental prosthetic appliance (e.g., a crown) made from the object exhibits good compatibility when the shape accuracy (dimensional error) is 5.0% or less.

$$\text{Shape accuracy (\%)} = \frac{|(\text{measured dimensions}) - 10.0|}{10.0} \times 100 \quad [\text{Math. 1}]$$

Transparency

The compositions of Examples and Comparative Example shown in Tables 1 and 2 were used to produce disc-shaped objects measuring 15.0 mm in diameter and 1.0 mm in thickness, using a stereolithography device (DigitalWax® 028J-Plus available from DWS). The object was washed with methanol, and, after removing unpolymerized monomers, was further polymerized for 90 seconds to obtain a cured product, using a dental LED polymerizer α-light V (available from Morita Tokyo MFG. Corp.). The cured product was polished first with a silicon carbide paper #1000, and then with a dental lapping film (available from 3M). After being kept in 37° C. water for 24 hours, the product was measured for transparency αL using a spectrocolorimeter SE2000 (Nippon Denshoku Industries Co., Ltd.) with D65 illuminant. Transparency ΔL is defined by the following formula. A transparency (ΔL) of 25 or more is needed to provide high aesthetics. The results are presented in Tables 1 and 2.

$$\Delta L = L*W - L*B$$

In the formula, L*W represents the lightness L* in the L*a*b* color system measured against a white background according to JIS Z 8781-4:2013, and L*B represents the lightness L* in the L*a*b* color system measured against a black background.

Flexural Strength, and Flexural Modulus

The compositions of Examples and Comparative Example shown in Tables 1 and 2 were used to produce rectangular objects measuring 25.0 mm in length, 2.0 mm in width, and 2.0 mm in thickness, using a stereolithography device (DigitalWax® 028J-Plus available from DWS). The object was washed with methanol, and, after removing unpolymerized monomers, was further polymerized for 90 seconds to obtain a cured product, using a dental LED polymerizer α-light V (available from Morita Tokyo MFG. Corp.). The cured product was then polished with a silicon carbide paper #3000. After being kept in 37° C. water for 24 hours, the product was measured for flexural strength and flexural modulus using a universal precision tester (product code AGI-100, available from Shimadzu Corporation) at a crosshead speed of 1 mm/min with a 20-mm distance set between supports. The cured product was deemed as having desirable strength when it had a flexural strength of 100 MPa or more, and a flexural modulus of 5.0 GPa or more.

TABLE 1

|  |  | Examples | | | | | | | | |
|---|---|---|---|---|---|---|---|---|---|---|
|  |  | 1 | 2 | 3 | 4 | 5 | 6 | 7 | 8 | 9 |
| Raw materials (parts by mass) | UDMA (a)-1 | 70 | 70 | 70 | 70 | 70 |  | 70 | 60 | 80 |
|  | D-2.6E (a)-2 |  |  |  |  |  | 70 |  |  |  |
|  | TEGDMA (a)-3 |  |  |  |  |  |  | 30 |  |  |
|  | ACMO (a)-4 | 30 | 30 | 30 | 30 | 30 | 30 |  | 40 | 20 |
|  | Inorganic particle (b)-1 | 100 |  |  | 50 | 250 | 100 | 100 | 100 | 100 |
|  | Inorganic particle (b)-2 |  | 100 |  |  |  |  |  |  |  |
|  | Inorganic particle (b)-3 |  |  | 100 |  |  |  |  |  |  |
|  | TPO (e)-1 | 3.0 | 3.5 | 3.0 | 3.0 | 3.0 | 3.0 | 3.0 | 3.0 | 2.0 |
|  | HOB (d)-1 | 0.05 | 0.10 | 0.05 | 0.05 | 0.05 | 0.05 | 0.05 | 0.05 | 0.01 |
|  | BHT | 0.05 | 0.05 | 0.05 | 0.05 | 0.05 | 0.05 | 0.05 | 0.05 | 0.05 |
| Properties | Shape accuracy (%) | 3.0 | 4.6 | 3.5 | 4.8 | 2.4 | 3.2 | 3.3 | 3.6 | 3.2 |
|  | Transparency (ΔL) | 40 | 52 | 35 | 55 | 32 | 38 | 40 | 38 | 40 |
|  | Flexural strength (MPa) | 105 | 110 | 120 | 102 | 124 | 110 | 102 | 102 | 110 |
|  | Flexural modulus (GPa) | 5.5 | 6.3 | 6.0 | 5.2 | 6.5 | 6.0 | 5.8 | 5.4 | 5.8 |

TABLE 2

|  |  |  | Comparative Example 1 |
|---|---|---|---|
| Raw materials (parts by mass) | UDMA | (a)-1 | 70 |
|  | ACMO | (a)-4 | 30 |
|  | TPO | (c)-1 | 3.0 |
|  | HOB | (d)-1 | 0.05 |
|  | BHT |  | 0.05 |
| Properties | Shape accuracy (%) |  | 10 |
|  | Transparency (ΔL) |  | 55 |
|  | Flexural strength (MPa) |  | 78 |
|  | Flexural modulus (GPa) |  | 2.6 |

As can be seen in Tables 1 and 2, the compositions for optical three-dimensional modeling of Examples 1 to 9 had desirable shape accuracy, and the cured products were desirable in transparency, flexural strength, and flexural modulus. The compositions for optical three-dimensional modeling of Examples 1 to 9 were more desirable particularly in shape accuracy than the composition for optical three-dimensional modeling of Comparative Example 1.

INDUSTRIAL APPLICABILITY

The composition for optical three-dimensional modeling of the present invention has desirable shape accuracy, and provides desirable mechanical characteristics and transparency when formed into a product by optical three-dimensional modeling. This makes the composition for optical three-dimensional modeling of the present invention particularly suitable as a dental material. The cured product in its three-dimensional form also has desirable transparency, and satisfies the aesthetic quality needed for dental restorative material applications. This makes the cured product particularly suitable as a dental restorative material (dental prosthetic appliance).

The invention claimed is:

1. A composition for optical three-dimensional modeling, comprising:
   a polymerizable monomer (a);
   an ultraviolet-absorbing inorganic particle (b);
   a photopolymerization initiator (c); and
   an organic ultraviolet absorber (d),
   wherein the ultraviolet-absorbing inorganic particle (b) is surface-treated with a surface treatment agent.

2. The composition for optical three-dimensional modeling according to claim 1, wherein the organic ultraviolet absorber (d) comprises a benzotriazole compound.

3. The composition for optical three-dimensional modeling according to claim 1, wherein the polymerizable monomer (a) comprises a (meth)acrylate polymerizable monomer and/or a (meth)acrylamide polymerizable monomer.

4. The composition for optical three-dimensional modeling according to claim 1, wherein the polymerizable monomer (a) comprises an aliphatic difunctional (meth)acrylate polymerizable monomer, or an aromatic difunctional (meth)acrylate polymerizable monomer.

5. The composition for optical three-dimensional modeling according to claim 1, wherein the polymerizable monomer (a) comprises a monofunctional (meth)acrylamide polymerizable monomer.

6. The composition for optical three-dimensional modeling according to claim 1, wherein the ultraviolet-absorbing inorganic particle (b) comprises at least one ultraviolet-absorbable inorganic compound selected from the group consisting of zinc oxide, cerium oxide, europium oxide, and zirconium oxide.

7. The composition for optical three-dimensional modeling according to claim 1, wherein the ultraviolet-absorbing inorganic particle (b) comprises zinc oxide and/or cerium oxide.

8. The composition for optical three-dimensional modeling according to claim 1, wherein the ultraviolet-absorbing inorganic particle (b) has an average primary particle diameter of 500 nm or less.

9. The composition for optical thee-dimensional modeling according to claim 1, wherein the composition comprises the ultraviolet-absorbing inorganic particle (b) in an amount of 50 to 400 parts by mass relative to total 100 parts by mass of the polymerizable monomer (a).

10. A dental material formed of a cured product of the composition for optical three-dimensional modeling of claim 1.

11. A method for producing a three-dimensional object by optical three-dimensional modeling using the composition for optical three-dimensional modeling of claim 1.

12. The composition for optical three-dimensional modeling according to claim 1, wherein
   the polymerizable monomer (a) comprises a monofunctional (meth)acrylamide polymerizable monomer,
   the ultraviolet-absorbing inorganic particle (b) comprises at least one ultraviolet-absorbable inorganic compound selected from the group consisting of zinc oxide, cerium oxide, europium oxide, and zirconium oxide,
   the photopolymerization initiator (c) is 2,4,6-trimethylbenzoyldiphenylphosphine oxide, and
   the organic ultraviolet absorber (d) is 2-hydroxy-5-tert-octylphenyl)benzotriazole.

* * * * *